(12) United States Patent
Rankin

(10) Patent No.: US 8,282,499 B2
(45) Date of Patent: *Oct. 9, 2012

(54) METHOD AND APPARATUS FOR MEASURING GOLF GREEN SPEEDS

(75) Inventor: David B. Rankin, Winston-Salem, NC (US)

(73) Assignee: Callaway Golf Company, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/307,833

(22) Filed: Nov. 30, 2011

(65) Prior Publication Data

US 2012/0077608 A1    Mar. 29, 2012

Related U.S. Application Data

(63) Continuation of application No. 12/464,704, filed on May 12, 2009, now Pat. No. 8,070,620.

(60) Provisional application No. 61/052,343, filed on May 12, 2008, provisional application No. 61/052,314, filed on May 12, 2008.

(51) Int. Cl.
*A63F 13/00* (2006.01)
*G01P 15/00* (2006.01)

(52) U.S. Cl. .................. 473/222; 463/2; 463/7; 473/198

(58) Field of Classification Search .................. 473/198, 473/222; 463/2, 7
See application file for complete search history.

*Primary Examiner* — Peter DungBa Vo
*Assistant Examiner* — Jeffrey Wong
(74) *Attorney, Agent, or Firm* — Michael A. Catania; Sonia Lari; Rebecca Hanovice

(57) ABSTRACT

A method, system and golf ball are provided to determine the deceleration of a golf ball and, in turn, the speed of a green. The system may include a golf ball and an offboard display device. The golf ball may include a golf ball body, a motion sensor disposed within the golf ball body to measure acceleration of the golf ball along each of three mutually perpendicular axes, and a transmitter disposed within the golf ball body to transmit data representative of deceleration. The display device may include a receiver to receive data representative of the deceleration of the golf ball from transmitter and a display to provide a representation of the deceleration of the golf ball. At least one of the golf ball and the display device may include a processor to determine deceleration of the golf ball based upon the acceleration measured by the motion sensor.

10 Claims, 3 Drawing Sheets

METHOD AND APPARATUS FOR MEASURING GOLF GREEN SPEEDS

CROSS REFERENCES TO RELATED APPLICATIONS

The present application is a continuation application of U.S. patent application Ser. No. 12/464,704, filed on May 12, 2009, which claims priority to provisional applications bearing Application Nos. 61/052,343 and 61/052,314 filed May 12, 2009, the contents of all are incorporated herein by reference in their entireties.

STATEMENT REGARDING FEDERALLY SPONSORED RESEARCH OR DEVELOPMENT

Not Applicable

BACKGROUND OF THE INVENTION

1. Field of the Invention

A method and apparatus are provided according to embodiments of the present invention in order to assessing the "speed" of a golf course putting green or hole. In this regard, the "speed" may be an indication of the rate of deceleration of the ball as it is rolling over the green.

2. Description of the Related Art

Many factors such as grass type, cut height, water content of the leaf, moisture content of the ground, air temperature and humidity, etc. have an impact on this quality of the ball roll. Furthermore, all of these factors can change from hole to hole and over the course of a few minutes. For a golfer, understanding this measurement is critical to accurate putting as it is a primary factor in determining the strength of a desired putting stroke.

Many mechanical systems have been used in the past, each with significant limitations or flaws. The most common method rolls a ball down a portable ramp onto the green and this rollout distance is measured. This is done in several different directions to account for any slope in the green and the numbers are combined to compute a "green speed". This method is very inconvenient for a golfer to user, it is prone to errors if used improperly and it cannot be used at all in areas with steep grades to the green.

BRIEF SUMMARY OF THE INVENTION

A method, system and golf ball are therefore provided in accordance with embodiments of the present invention in order to determine the deceleration of a golf ball and, in turn, the speed of a green. In one embodiment, a system includes a golf ball and an offboard display device. The golf ball may include a golf ball body, a motion sensor disposed within the golf ball body and configured to measure acceleration of the golf ball along each of three mutually perpendicular axes, and a transmitter disposed within the golf ball body and configured to transmit data representative of deceleration of the golf ball. In turn, the display device may include a receiver configured to receive data representative of the deceleration of the golf ball from transmitter and a display configured to provide a representation of a measure of the deceleration of the golf ball. In this embodiment, at least one of the golf ball and the display device may include a processor configured to determine deceleration of the golf ball based upon the acceleration measured by the motion sensor.

In order to determine the deceleration, the processor of one embodiment is configured to determine a distance rolled by the golf ball and a time elapsed during rolling of the golf ball. The processor of this embodiment is then configured to determine the deceleration based upon the distance rolled and the time elapsed. Also, the processor may be further configured to determine a number of cycles of a sine wave signal provided by the motion sensor with the processor's determination of the distance rolled being based upon the number of cycles.

In addition to the system described above, a method and a golf ball, including an embedded processor, are also provided in accordance with other embodiments in order to determine the deceleration of the golf ball and, in turn, the speed of a green.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Figure 1:
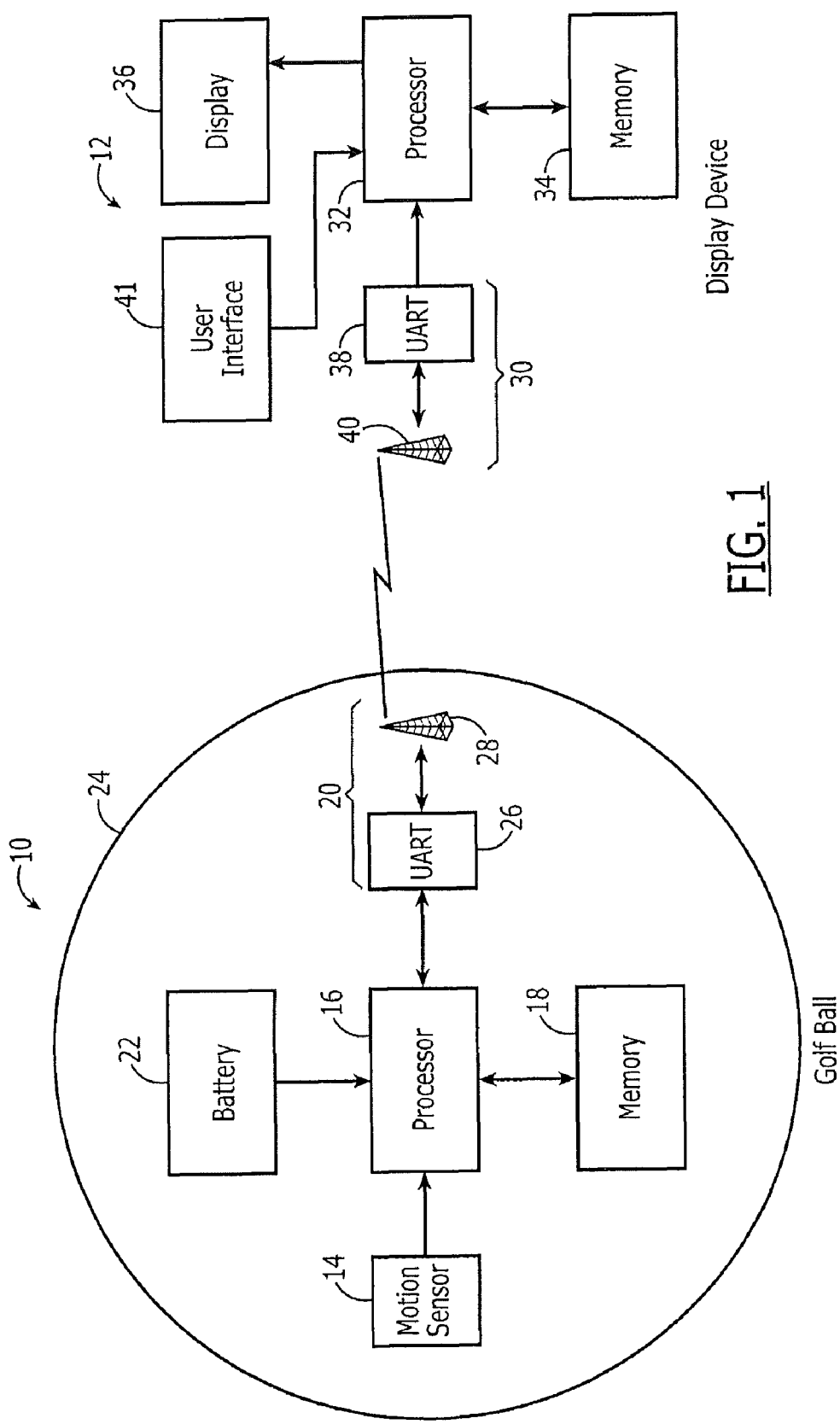
FIG. 1 is a block diagram of a system in accordance with one embodiment of the present invention.

The system consists of a modified golf ball 10 and a display device 12 configured to communicate with one another, typically in a wireless manner. The golf ball of one embodiment has a motion sensor 14, processor 16, memory 18, radio 20 and power system 22 embedded into the body 24 of the golf ball. In one embodiment, the embedded components weigh only about 1 gram so as not to meaningfully alter the performance of the golf ball. As shown in FIG. 1, the motion sensor may be three-axis accelerometer configured to repeatedly provide a three-dimensional vector indicative of the current acceleration acting upon the ball in three orthogonal directions, e.g., the x, y and z directions. Other types of motion sensors can employed including, for example, magnetometers, if so desired. The output of the accelerometer may be provided to an analog-to-digital converter for converting the signals representative of the current acceleration to digital values which, in turn, are provided to the processor.

The processor 16 includes or is otherwise associated with a clock and, as such, associates a time with each set of acceleration values provided by the motion sensor 14 and stores the acceleration values in memory 18. By storing the acceleration values over time, the processor can also integrate the acceleration along each of the three orthogonal axes in order to determine the velocity of the golf ball 10 along each of the three orthogonal axes. The processor can further integrate the velocity along each of the three orthogonal axes in order to determine the position of the ball along each of the three orthogonal axes. As described below, the processor can further process the acceleration values and analyze the results depending upon the desired output. The processor can also cause the results to be transmitted to the offboard display device 12. In this regard, the radio 20 of the golf ball may also include a transmitter or a transceiver and an associated antenna, such as a single chip 802.15.4 low-power digital data radio, for providing a wireless transmission to the display device. As shown in FIG. 1, for example, the radio of the golf ball may include a universal asynchronous receiver/transmitter (UART) 26 and an associated antenna 28 for supporting the wireless communication with the display device. As to the power system 22, the golf ball may include an onboard battery which may, in one embodiment, be wirelessly recharged. For example, the battery may be a CR2032 battery or the like. Alternatively, the electronics of the golf ball may operate passively with energy provided from an external source.

The display device 12 also generally consists of a radio 30, processor 32, memory 34 and a display 36, such as an LCD display. As described in conjunction with the golf ball 10, the radio of the display device may also include a transmitter or a transceiver and an associated antenna for receiving wireless transmissions from the golf ball. As shown in FIG. 1, for example, the radio of the display device may include a universal asynchronous receiver/transmitter (UART) 38 and an associated antenna 40 for supporting the wireless communication with the golf ball. The processor of the display device can provide for storage of the information provided by the golf ball and can appropriately drive the display in order to provide at least some of the information received from the golf ball to the user. If desired, the display device may include a user interface 41 for permitting the user to provide input regarding the information to be presented and/or the format of the information to be presented. Further, the display device may include an interface, such as a USB interface, a BlueTooth interface or the like, for permitting the information provided by the golf ball and stored by the display device to be downloaded to a computer. Further, while the system of one embodiment is described herein such that the processor of the golf ball performs the analysis of the data provided by the motion sensor, the processing responsibilities can be differently divided with the processor of the display device performing some or all of the analysis.

In operation, the user can roll the ball 10 across the green and when the processor 16 of the ball determines that the ball is rolling along the ground (as opposed to being stationary or bouncing), the processor measures the output of the motion sensor 14 at a predetermined rate, such as 1000 times per second, until the processor determines the motion has completed. With this data, the processor is able to make a detailed analysis of the deceleration of the ball as it rolls along the ground. If desired, the user can roll the ball in multiple directions with the processor separately monitoring the motion in each direction to obtain a set of measurements. In either case, this information is used by the processor of the ball to compute an accurate assessment of the green speed, which is transmitted to the display device. Furthermore, the processor 32 in the display device 12 can use the data to provide a historical analysis of each hole, such as a comparison of the current green speed to the last time the golfer played the course.

Figure 2:
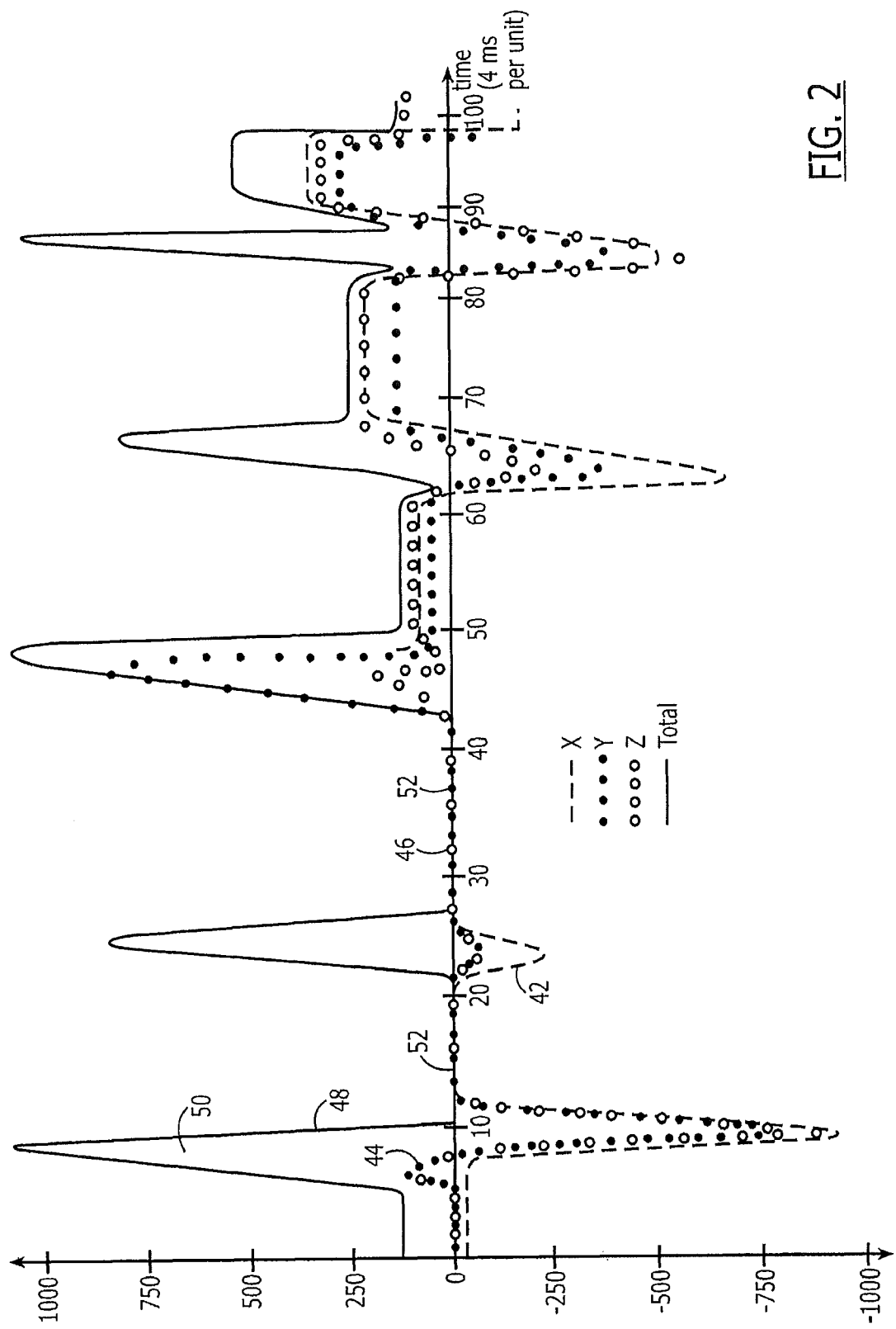
FIG. 2 is an example of a waveform produced by a motion sensor in accordance with one embodiment of the present invention.

As the ball 10 is struck, moving and rolling, three forces act on the accelerometer 14, namely, gravity, impact and rotation, with the accelerometer providing the vector sum of these three forces, that is, the square root of $a_x^2 + a_y^2 + a_z^2$ wherein $a_x$, $a_y$ and $a_z$ are the accelerations in the x, y and z axes, respectively. As shown in the example of FIG. 2, the sensor, such as an accelerometer, provides a measurement of the acceleration along each axis of the sensor, designated the x, y and z axes and identified as 42, 44 and 46, respectively, in FIG. 2. The thick line 48 is the computed magnitude of all three axes when treated as a vector, that is, the square root of $a_x^2 + a_y^2 + a_z^2$. The first spike 50 on the left side of FIG. 2 is the putting stroke. The shape of this spike indicates the nature of the impact between the ball and the club. Following the impact spike, the ball generally enters a phase of zero magnitude indicating that the ball is in flight. While this is difficult to directly observe, nearly every putt has moments of flight. In this case, the plot shows two such segments 52; 11 to 21 and 25 to 43. The duration and number of the flights are used to determine the "bounciness" of the ball as it is transitioning to a pure roll condition. Each subsequent spike caused by the ball impacting the ground. During this time, the output of the motion sensor is treated as a vector (direction and magnitude) that is normalized, such as by means of a Rodrigues transform, in comparison to the "at=rest" vector at the moments prior to the start of the putt. As the ball begins to roll forward, centripetal forces start to act on the motion sensor, as well as gravity. These two components combine to create a signal on each axis consisting of a sine wave attributable to gravity with an offset due to centripetal force, as shown, for example, in FIG. 3 in which that portion 54 of the waveform of FIG. 2 along one axis is enlarged for purposes of illustration. The frequency and duration of the sine wave can be used to measure the speed and distance the ball is traveling. In this regard, the acceleration signals as measured along each axis will produce a sine wave as the ball rotates relative to gravity.

Figure 3:
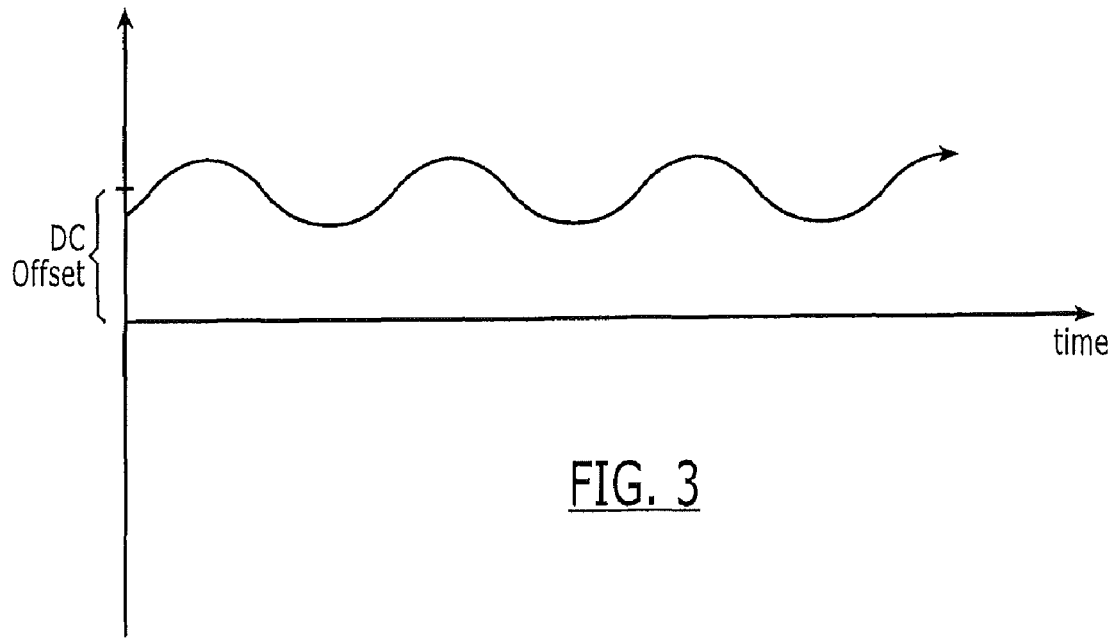
FIG. 3 is an enlarged portion of the waveform of FIG. 2 for one axis during which the golf ball is rolling.

In one embodiment, after the ball 10 is rolled onto the ground, the initial readings of the motion sensor 14 are ignored by the processor 16, allowing the ball to transition from the initial bouncing and/or skidding to a smooth roll. While the determination that the ball is smoothly rolling may be done in various manners, it is noted that a bounce generally has much higher frequency components (such as 50 to 100 Hertz) as opposed to rolling (such as 1 Hertz). As such, the processor may analyze the acceleration and identify the ball to be rolling once the frequency is less than a predefined value, such as 10 or 20 Hertz. As the ball begins to roll forward, centripetal forces start to act on the motion sensor, as well as gravity. These two components combine to create a signal on each axis of the motion sensor consisting of a sine wave from gravity with an offset due to centripetal force. By way of example and in order to demonstrate the sine wave, FIG. 3 is an enlarged representation of a portion of the curve shown in FIG. 2 along the x-axis during which the golf ball is rolling. The frequency and duration of the sine wave can be used by the processor to measure the speed and distance the ball is traveling. In this regard, the acceleration signals as measured along each axis will produce a sine wave as the ball rotates relative to gravity. When the axis is normal to the ground, the accelerometer will sense nearly 0 g. When the axis is pointed down, the accelerometer will sense nearly 1 g and conversely when the accelerometer is pointed straight up, it will sense −1 g. If the axis is not perfectly parallel or normal to the gravity vector, the accelerometer will sense a value that is related to 1 g*cos (tilt angle (e.g., angle relative to the gravity vector)).

Figure 4:
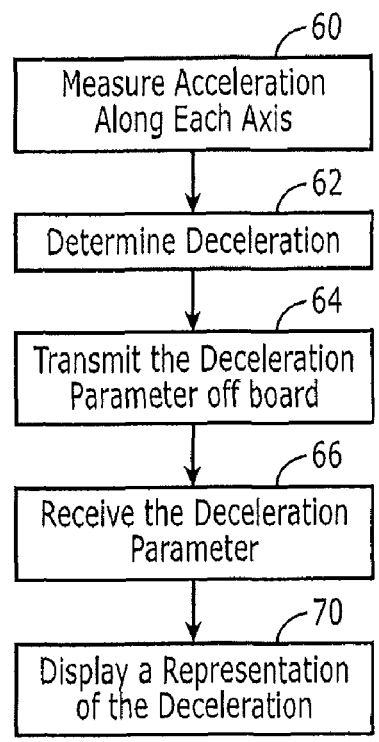
FIG. 4 is a flow chart of operations performed in accordance with embodiments of the present invention.

As such, when the ball 10 is rotating, the acceleration signals as measured along each axis as indicated by block 60 of FIG. 4 will be a sine wave. For the purposes of measuring RPM and distance rolled (e.g., from the onset of rolling as described above to the cessation of rolling as indicated by the acceleration going to zero), it is not necessary to measure the amplitude of the sine wave just the frequency. If a ball rolls 10 feet, it would be expected that the number of sine waves would equal 120"/(1.68"*pi). Conversely, if the number of sine waves is known and is denominated as wavecnt, the processor 16 can determine the rolling distance by: (1.68"*pi) *wavecnt. Once the distance is determined, the processor can determine the speed by dividing the distance by the time taken to traverse the distance. As the frequency of the sine wave increases or decreases, indicating acceleration or deceleration, respectively, the processor is therefore able to measure the actual change in speed of the ball. This only works for the portion of the putt where the ball is rolling. Prior to that, when the ball is sliding, the processor may double integrate the acceleration vectors to compute the distance. Since the motion sensor 14 may not be at the precise center of gravity, centripetal force will add a DC offset to the sine wave. As such, the golf ball may include a digital high pass filter to subtract this DC offset from the signal.

The processor 16 is able to determine the deceleration by determining the rate at which the magnitude of the total acceleration decreases over at least a portion of the period during which the golf ball 10 is rolling. See block 62 of FIG. 4. For example, by looking at the smoothness of the acceleration signals, the processor of one embodiment is able to find the most consistent segment of the roll, preferably of at least a predetermined minimum duration, to obtain the deceleration measurement, such as the rate at which the magnitude of the total acceleration decreases. As noted above, the deceleration is a measure of the speed of a green.

It is noted that the deceleration of a putt ball is not linear in nature but the deceleration varies with the descending speed of the ball. In other words, the so-called speed of a green is actually significantly variable over a range of speeds. As such, the processor 16 of one embodiment is configured to not only determine the average acceleration, but to also determine the shape of the deceleration by determining both the velocity (e.g., ball rolling or putt speed) and the corresponding deceleration of the ball at the respective velocity at each of a plurality of different locations or within each of a number of different regions along the ball's path. For example, the processor may determine a first deceleration value for a ball at a first velocity shortly after impact, a second deceleration value for the ball at a second velocity during an intermediate portion of the ball's path and a third deceleration value for the ball at a third velocity near the end of the ball's path. As will be apparent, the first velocity is generally greater than the second velocity, and the second velocity is generally greater than the third velocity since the ball is decelerating along the path. By determining the deceleration at each of a number of velocities, the system of this embodiment provides additional information to a golfer in the form of the green speed at a number of different velocities. By communicating the variability of the deceleration (or green speed) to the golfer, the golfer may have a greater understanding of the how the green conditions will affect the putt they are about to attempt.

Once the deceleration is determined, the processor 16 of the golf ball 10 may provide the deceleration to the display device 12 for presentation to the user, either alone or in comparison to historical information regarding the deceleration value of the green in the past. See blocks 64, 66 and 68 of FIG. 4.

In most cases, the deceleration value is reasonably independent of the slope of the ground; this is a great advantage of directly measuring deceleration rather than total roll distance. However, in cases of extreme slope, it may be advantageous to make several measurements in different directions and combine them, such as by averaging them or otherwise combining them in a manner that is acceptable to the golf industry.

Finally, the obtained value of deceleration is in units of meters per second squared. To aid in at least initial comprehension, this unit of measure may be presented along with a more familiar green speed value. This requires that the measured deceleration be scaled to a value that is currently in use in the golf industry with this scaling factor likely being determined by experimentation.

The respective processors 14, 32 of the golf ball 10 and the display device 12 may perform the above-described method under control of a computer program product that may be stored, for example, by the associated memory device 18, 34. For example, one or more of the procedures described above may be embodied by computer program instructions. As will be appreciated, any such computer program instructions may be loaded into the memory and, in turn, the associated processor to produce a machine, such that the instructions which execute on the processor create means for implementing the functions specified in the flowcharts block(s) or step(s). These computer program instructions may also be stored in a computer-readable memory that can direct a processor or other programmable apparatus to function in a particular manner, such that the instructions stored in the computer-readable memory produce an article of manufacture. The computer program instructions may also be loaded onto a processor or other programmable apparatus to cause a series of operational steps to be performed on the processor or other programmable apparatus to produce a computer-implemented process.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

I claim as my invention the following:
1. A system comprising:
 a golf ball comprising
  a golf ball body,
  a motion sensor disposed within the golf ball body and configured to measure acceleration of the golf ball along each of three mutually perpendicular axis,
  a processor configured to determine a deceleration of the golf ball based upon the acceleration measured by the motion sensor, and wherein the processor is also configured to determine a frequency of signals provided by the motion sensor and to await the frequency falling below a predefined threshold prior to determining a deceleration of the golf ball,
  a transmitter disposed within the golf ball body configured to transmit data representative of deceleration of the golf ball; and
 a display device comprising,
  a receiver configured to receive data representative of the deceleration of the golf ball from transmitter, and
  a display configured to provide a representation of a measure of the deceleration of the golf ball.
2. A system according to claim 1 wherein the processor is configured to determine a distance rolled by the golf ball and a time elapsed during rolling of the golf ball, and wherein the processor is configured to determine the deceleration based upon the distance rolled and the time elapsed.

3. A system according to claim 1 wherein the processor is further configured to determine a number of cycles of a sine wave signal provided by the motion sensor, and wherein the processor is configured to determine the distance rolled based upon the number of cycles.

4. A system according to claim 1 further comprising a filter configured to remove a DC offset from a signal provided by the motion sensor prior to determination of the deceleration by the processor.

5. A system according to claim 1 wherein the processor, is further configured to determine a plurality of deceleration values with each deceleration value being associated with a different respective velocity of the golf ball.

6. A system comprising:
   a golf ball comprising
      a golf ball body,
      a motion sensor disposed within the golf ball body and configured to measure acceleration of the golf ball along each of three mutually perpendicular axis,
      a transmitter disposed within the golf ball body configured to transmit data representative of deceleration of the golf ball; and
   a display device comprising,
      a receiver configured to receive data representative of the deceleration of the golf ball from transmitter,
      a processor configured to determine a deceleration of the golf ball based upon the acceleration measured by the motion sensor, and wherein the processor is also configured to determine a frequency of signals provided by the motion sensor and to await the frequency falling below a predefined threshold prior to determining a deceleration of the golf ball, and
      a display configured to provide a representation of a measure of the deceleration of the golf ball.

7. A system according to claim 6 wherein the processor is configured to determine a distance rolled by the golf ball and a time elapsed during rolling of the golf ball, and wherein the processor is configured to determine the deceleration based upon the distance rolled and the time elapsed.

8. A system according to claim 6 wherein the processor is further configured to determine a number of cycles of a sine wave signal provided by the motion sensor, and wherein the processor is configured to determine the distance rolled based upon the number of cycles.

9. A system according to claim 6 further comprising a filter configured to remove a DC offset from a signal provided by the motion sensor prior to determination of the deceleration by the processor.

10. A system according to claim 6 wherein the processor is further configured to determine a plurality of deceleration values with each deceleration value being associated with a different respective velocity of the golf ball.

* * * * *